United States Patent [19]

Kobayashi et al.

[11] Patent Number: 4,957,853
[45] Date of Patent: * Sep. 18, 1990

[54] SILVER HALIDE COLOR PHOTOGRAPHIC LIGHT-SENSITIVE MATERIAL CONTAINING CYAN COUPLER AND METHOD FOR USE THEREOF

[75] Inventors: Hidetoshi Kobayashi; Toshihiro Nishikawa, both of Kanagawa, Japan

[73] Assignee: Fuji Photo Film Co., Ltd., Kanagawa, Japan

[*] Notice: The portion of the term of this patent subsequent to Jun. 6, 2006 has been disclaimed.

[21] Appl. No.: 149,040

[22] Filed: Jan. 27, 1988

Related U.S. Application Data

[63] Continuation-in-part of Ser. No. 917,116, Oct. 8, 1986, abandoned.

[30] Foreign Application Priority Data

Oct. 8, 1985 [JP] Japan ................... 60-224345

[51] Int. Cl.$^5$ ............................. G03C 7/34
[52] U.S. Cl. ..................... 430/384; 430/385; 430/552; 430/553
[58] Field of Search ............. 430/384, 385, 552, 553

[56] References Cited

U.S. PATENT DOCUMENTS

| | | | |
|---|---|---|---|
| 3,469,986 | 9/1969 | Yoshida et al. | 430/553 |
| 3,488,193 | 1/1970 | Vanden Eynde et al. | 430/553 |
| 3,556,796 | 1/1971 | Vanden Eynde et al. | 430/553 |
| 3,622,337 | 11/1971 | Altavilla | 430/553 |
| 3,892,576 | 7/1975 | Van Poucke et al. | 430/554 |
| 4,725,530 | 2/1988 | Kobayashi et al. | 430/505 |
| 4,737,451 | 4/1988 | Ichijima | 430/544 |
| 4,837,136 | 6/1989 | Ichijima et al. | 430/543 |

Primary Examiner—Paul R. Michl
Assistant Examiner—Lee C. Wright
Attorney, Agent, or Firm—Sughrue, Mion, Zinn, Macpeak & SEas

[57] ABSTRACT

A novel silver halide color photographic light-sensitive material is provided having at least one light-sensitive silver halide emulsion layer provided on a support and said photographic material contains at least one cyan dye-forming coupler represented by formula (I)

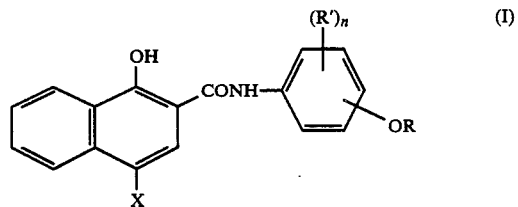

wherein r represents a substituted or unsubstituted branched alkyl or substituted alkyl group containing 6 or more carbon atoms; X represents a hydrogen atom or a non-photographically-useful group which can be released therefrom upon coupling with an oxidized form of an aromatic primary amine developing agent; R' represents a group which can be substituted at a phenyl nucleus other than a group which can be represented by OR; and n is an integer of from 0 to 4.

15 Claims, No Drawings

SILVER HALIDE COLOR PHOTOGRAPHIC LIGHT-SENSITIVE MATERIAL CONTAINING CYAN COUPLER AND METHOD FOR USE THEREOF

This is a continuation-in-part, of application Ser. No. 06/917,116 filed Oct. 8, 1986, now abandoned.

FIELD OF THE INVENTION

The present invention relates to a silver halide color photographic material. More particularly, the present invention relates to a silver halide color photographic material which provides a high sensitivity, excellent color reproducibility, and improved processability by the use of a novel cyan dye-forming coupler (hereinafter referred to as "cyan coupler").

BACKGROUND OF THE INVENTION

When a silver halide color photographic material is subjected to color development after being exposed to light, the resulting oxidized aromatic primary amine developing agent reacts with a dye-forming coupler to form a color image. In general, this process uses color reproduction by subtractive process. In order to reproduce blue, green, and red, color images of yellow, magenta, and cyan, which are their respective complementary colors, are formed. For the formation of a cyan color image, a phenol derivative or naphthol derivative is often used as a coupler. In color photography, a color-forming coupler is added to a developing solution or incorporated in a light-sensitive photographic emulsion layer or other color image-forming layers. Such a color-forming coupler reacts with an oxidized form of a color developing agent formed upon development to form a nondiffusive dye.

The reaction of a coupler with a color developing agent takes place at the active position of the coupler. The coupler containing a hydrogen atom at the active position is a tetraequivalent coupler, i.e., coupler which stoichiometrically needs 4 moles of a silver halide containing development nuclei to form 1 mole of dye. On the other hand, the coupler containing a releasable group as anion at the active position is a diequivalent coupler, i.e., coupler which stoichiometrically needs only 2 moles of silver halide containing development nuclei to form 1 mole of dye. Accordingly, as compared to tetraequivalent coupler, the use of such a diequivalent coupler can reduce the amount of silver halide required to be contained in the light-sensitive layer, providing a thinner film. This enables a reduction in the time for processing of the light-sensitive material and improves the sharpness of color images formed.

As such a cyan dye-forming coupler there has been heretofore used a phenol or naphthol coupler. In particular, a naphthol coupler is advantageous in that the dye produced thereby has a maximum absorption ($\lambda_{max}$) of a longer wavelength. This means that the coupler absorbs less light in the green region, thus providing excellent color reproducibility. Furthermore, a large number of couplers excellent in color-forming properties have been found and put into practical use, particularly as color negative light-sensitive material.

However, most of such naphthol couplers, particularly 2-alkylcarbamoyl-1-naphthol coupler, or such phenol couplers are disadvantageous in that when processed with a fatigued bleaching or blix bath or a bleaching or blix bath having a weak oxidizing power in a bleaching or blix process in color development processings, they cannot provide a sufficient color image density. This phenomenon is thought to be partially attributable to discoloration of the cyan dye by ferrous ions produced bleaching or blix process.

In order to eliminate such a disadvantage, phenol couplers containing a ureido group at the 2-position and a carboamido group at the 5-position have been proposed. Examples of such phenol couplers are disclosed in U.S. Pat. Nos. 4,333,999, 4,451,559, 4,465,766, and 4,427,767 and Japanese Patent Application (OPI) Nos. 65134/81, 204543/82, 204544/82, 204545/82, 33249/83, and 33250/83 (the term "OPI" as used herein means an "unexamined published application"). These couplers are advantageous in that they are less susceptible to discoloration of color images by ferrous ions and that color images formed thereby are fast to light, heat, and moisture. However, on the other hand, these couplers are also disadvantageous in that the color images formed thereby absorb more light in the green region, thus providing poor color reproduction. Furthermore, since these couplers do not have sufficient color formation properties, they are not always suitable for the recent high sensitivity light-sensitive materials excellent in image quality.

2-arylcarbamoyl-1-naphthol couplers as described in U.S. Pat. No. 3,488,193 are advantageous in that color images formed thereby absorb less light in the green region, that the color images thus formed are less susceptible to discoloration by ferrous ions, and that they are excellent in color formation properties. As a 2-arylcarbamoyl-1-naphthol coupler there have been heretofore known those containing straight-chain alkoxy groups as the substituent or ballast group (also called anti-diffusion group) for the aryl group at the 2-position of 1-naphthol as described in U.S. Pat. No. 3,488,193. However, these couplers are disadvantageous in that color images formed thereby have a maximum absorption wavelength ($\lambda_{max}$) shifted to remarkably short wavelength in a higher color density region or higher dye density region. This increases the absorption of light in the green region, deteriorating the color reproducibility.

Furthermore, coupler containing a branched alkoxy group as an anti-diffusion group are disclosed in Japanese Patent Application (OPI) No. 3031/73 corresponding to U.S. Pat. No. 3,892,576. However, neither description nor suggestion of application to 2-arylcarbamoyl-1-naphthol couplers is given in the above patent. The object of the coupler is to improve solubility and dispersibility of couplers.

SUMMARY OF THE INVENTION

It is therefore an object of the present invention to provide a silver halide color photographic material which shows an extremely small reduction in cyan color density when processed with a fatigued bleaching or blix bath or a bleaching or blix bath having a weak oxidizing power in bleaching or blix process.

It is another object of the present invention to provide a silver halide color photographic material which provides a high sensitivity and excellent image quality by the use of a novel cyan coupler excellent in color formation.

It is a further object of the present invention to provide a silver halide color photographic material which provides an excellent color reproducibility by the use of a novel cyan coupler which can form cyan color images having less absorption of light in the green region and which give a maximum absorption wavelength independent of color density.

These and other objects of the present invention will become more apparent from the following description and examples.

These objects of the present invention are accomplished by a silver halide color photographic light-sensitive material having at least one light-sensitive silver halide emulsion layer provided on a support, and said photographic material contains at least one non-diffusible. oil-soluble cyan dye-forming coupler of formula (I)

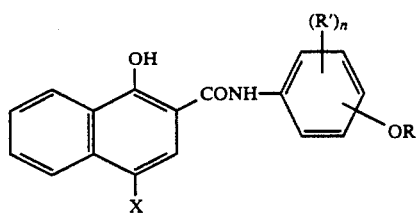

wherein R represents a substituted or unsubstituted branched alkyl group or an alkyl group substituted with other than an alkyl group, said R containing 6 or more carbon atoms and said R not being substituted with a carboxyl group, a sulfo group, a carboxyl group substituted with a metal atom or an —NH$_4$ group or a sulfo group substituted with a metal atom or an —NH$_4$ group; X represents a hydrogen atom or a non-photographically-useful group which can be released therefrom upon coupling with an oxidized form of an aromatic primary amine developing agent; R' represents a group which can be substituted at a phenyl nucleus other than a group which can be represented by OR; and n is an integer of from 0 to 4. said coupler being incorporated into the emulsion by an oil-in-water dispersion process.

As a result of extensive studies to solve the above-noted problems of 2-arylcarbamoyl-1-naphthol couplers, the inventors have found that these disadvantages can be eliminated by using a substituted or unsubstituted branched alkyl group or substituted alkyl group as the substituent R in formula (I). Surprisingly, the effects of such a substituent were much greater than expected.

DETAILED DESCRIPTION OF THE INVENTION

Compounds represented by formula (I) are described in more detail hereinafter.

In formula (I), R represents a substituted or unsubstituted branched alkyl group or an alkyl group substituted with other than an alkyl group, said R containing 6 or more carbon atoms. Specific examples of such a substituent include an alkenyl group, an alkynyl group. a cycloalkyl group, an aromatic group, a heterocyclic group, a halogen atom, an aliphatic oxy group, an aromatic oxy group, a heterocyclic oxy group, an aliphatic thio group, an aromatic thio group, a heterocyclic thio group, a hydroxy group, a cyano group, an aliphatic sulfonyl group, an aromatic sulfonyl group, a heterocyclic sulfonyl group, an aliphatic sulfinyl group, an aromatic sulfinyl group, a heterocyclic sulfinyl group, an aliphatic oxycarbonyl group, an acyloxy group, an acyl group, a carbamoyl group, a sulfamoyl group, a carbonamido group, a sulfonamido group, a ureido group, a sulfamoylamino group, an aliphatic oxycarbonylamino group, and a carbamoyloxy group. If the number of carbon atoms in R is 6 or more, the dye formed is rendered diffusion resistant. R does not have a carboxyl group or a sulfo group or a substituted group thereof with a metal atom, i.e.. R does not have —COOM— or —SO$_3$M (wherein M represents a hydrogen atom, a metal atom such as an alkali metal atom. e.g., Li, Na, and K, or NH$_4$; hereinafter M is defined as defined herein). The aliphatic moiety in the above-described groups is preferably an alkyl group having from 1 to 10 carbon atoms. Examples of preferable groups represented by R include an alkyl group substituted with at least one of an alkenyl group, a halogen atom, an aliphatic oxy group, an aliphatic thio group or an aliphatic oxycarbonyl group.

The terminal nitrogen atom of the above-described (and which are shown hereinafter) carbamoyl group, sulfamoyl group, ureido group, and sulfamoylamino group may be substituted with an aliphatic or aromatic hydrocarbon group. This hydrocarbon group may further substituted with a usual substituent such as an alkoxy group, a halogen atom, a cyano group, a hydroxy group, an acyl group, or an alkylthio group.

The above-described (and which are shown hereinafter) acyloxy group, acyl group, carbonamido group, and sulfonamido group contains an aliphatic or aromatic hydrocarbon group. This hydrocarbon group may further substituted with the above-described usual substituent.

X represents hydrogen atom or a group which can be released from the benzene ring upon coupling reaction with an oxidized form of aromatic primary amine developer (hereinafter referred to as "coupling-off group"). However, X is not a photographically useful group. Examples of such a coupling-off group include halogen atom, —COOM, —SO$_3$M, aliphatic oxy group, aromatic oxy group, heterocyclic oxy group, aliphatic thio group, aromatic thio group, acyl oxy group, carbonamido group, aliphatic sulfonyloxy group, aromatic sulfonyloxy group, aliphatic oxycarbonyloxy group, aliphatic thiocarbonylamino group, carbamoyloxy group, and heterocyclic group to be bonded to the coupling active position of a coupler by a nitrogen atom. Examples of photographically useful groups herein referred to include groups which, upon coupling, are released from the nucleus and then gives a photographic action (e.g., development inhibitor, development accelerator, silver halide solvent, developing agent, fogging agent, reducing agent, coupler, fog inhibitor, bleaching accelerator, bleaching inhibitor, and precursors thereof) and aromatic azo group used for color correcting colored coupler which shows an absorption in a specific visible range by bonding to a photographic dye and a coupler residue. The reason why a photographically useful group is not used as substituent X is as follows. That is, if a coupler containing a photographically useful group is added to the light-sensitive material in an amount such that its optimum effect can be obtained, the added amount is too small to provide the effects of the present invention. On the contrary, if the coupler is added to the light-sensitive material in an amount such that the effects of the present invention can be obtained, the added amount is too large to provide the desired effect, impairing the photographic properties.

In the above description, an aliphatic group represents a straight-chain, branched, or cyclic alkyl, alkenyl, or alkynyl group which may be substituted; an aromatic group represents a substituted or unsubstituted monocyclic or condensed aryl group; and a heterocyclic group represents a substituted or unsubstituted 5- or 6-membered monocyclic group containing at least one of an N, S, or O atom or condensed heterocyclic group thereof.

Examples for substituents for the aliphatic group include an aryl group, an alkoxy group, an epoxy group, a carbonamido group, a halogen atom, a cyano group, —COOM, a hydroxy group, a sulfonamido group, a carbonyl (including aliphatic and aromatic) group, an acyl group, an acyloxy group, an alkoxycarbonyl group, an alkylsulfonyl group, and aryloxy group.

Examples for substituents for the aryl groups include an alkyl group, an alkoxy group, an epoxy group, a carbonamido group, a halogen atom, a cyano group, —COOM, a hydroxy group, a sulfonamido group, a carbonyl (including aliphatic and aromatic) group, an acyl group, an acyloxy group, an alkoxycarbonyl group, an alkylsulfonyl group, and aryloxy group.

Examples for substituents for the heterocyclic group include an alkyl group, an aryl group, an alkoxy group, an epoxy group, a carbonamido group, a halogen atom, a cyano group, —COOM, a hydroxy group, a sulfonamido group, a carbonyl (including aliphatic and aromatic) group, an acyl group, an acyloxy group, an alkoxycarbonyl group, an alkylsulfonyl group, and aryloxy group.

Examples of such an aliphatic group include a methyl group, ethyl group, t-butyl group, cyclohexyl group, 2-ethylhexyl group, n-decyl group, n-dodecyl group, 2-hexyldecyl group, n-hexadecyl group, allyl group, propargyl group, benzyl group, octadecynyl group, trifluoromethyl group, carboxy methyl group, methoxyethyl group, dodecyloxy carbonyl methyl group, and 2-methyl sulfonyl ethyl group. Examples of an aromatic group include phenyl group, naphthyl group, p-tolyl group, 4-methoxyphenyl group, 2-acetamide phenyl group, and 4-t-octylphenyl group. Examples of such a heterocyclic group include 2-pyridyl group, 4-pyridyl group, 2-furyl group, 2-thienyl group, 8-quinolyl group, 1-phenyl-5-tetrazolyl group, 1-pyrazolyl group, 1-imidazolyl group, 2,4-dioxoimidazolidine-3-yl group, and benzotriazole-1-yl group. Among compounds represented by formula (I) those which are preferably used in the present invention are described below.

The group OR may be attached to any one of the ortho-position, meta-position, or para-position, preferably the ortho-position, with respect to the position of group —CONH in formula (I). The number of carbon atoms contained in R (including the substituent(s)) is preferably from 8 to 30. R is preferably a substituted or unsubstituted branched alkyl group, especially to attain the first object of the present invention.

X is preferably a hydrogen atom, chlorine atom, aliphatic oxy group, or aromatic oxy group. The number of carbon atoms contained in X is preferably not more than 30. Examples of substituents for the aliphatic group or the aromatic group include those described with reference to R.

Examples of aliphatic oxy groups for each X and R include methoxy group, ethoxy group, 2-chloroethoxy group, 2-hydroxyethoxy group, 2-methoxyethoxy group, carboxymethoxy group, 3-carboxypropyloxy group, 2-methoxyethoxycarbamoylmethoxy group, 1-carboxyethoxy group, 2-methylsulfonylethoxy group, 2-methylsulfoamidoethoxy group, 2-(carboxymethylthio)ethoxy group, and 3-(carboxymethylthio)propyloxy group. Examples of aromatic oxy groups for each X and R include 4-acetamidophenoxy group, 2-acetamidophenoxy group, 4-(3-carboxypropanamido)phenoxy group, and 4-methylsulfonylphenyl group. Further examples for R include 2-ethylhexyl, 2-hexyldecyl, 2-octyldodecyl, and 3-dodecylthiopropyl group.

Specific examples of R' are the same as the subsituents acceptable for R (except those represented by OR) and thus include the previously mentioned substituents from alkenyl group to carbamoyloxy group. A further example of R' is a halogen atom, such as chlorine, bromine, and fluorine atoms. R' may be substituted at either the m-, o-, or p-position.

n is preferably 0 or 1.

Examples of compounds represented by formula (I) are shown below.

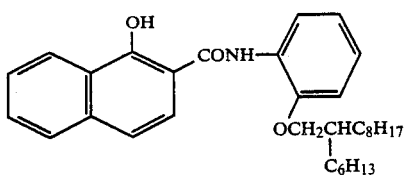

(1)

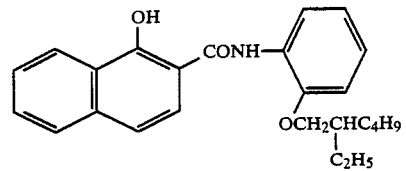

(2)

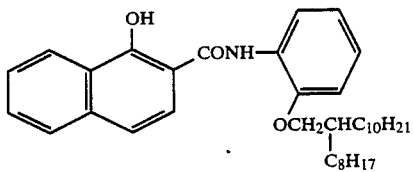

(3)

-continued
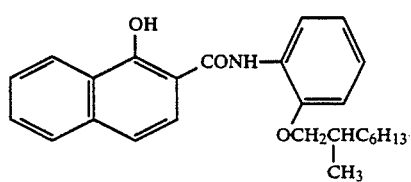 (4)
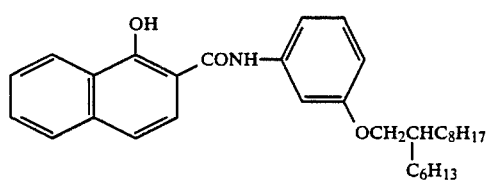 (5)
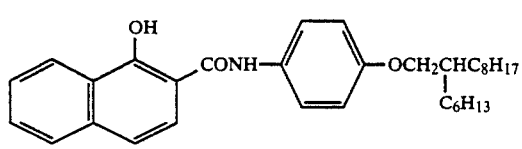 (6)
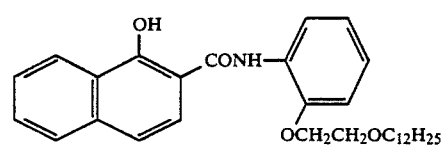 (7)
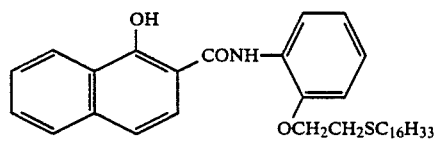 (8)
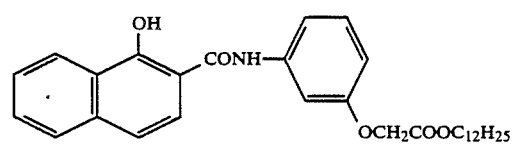 (9)
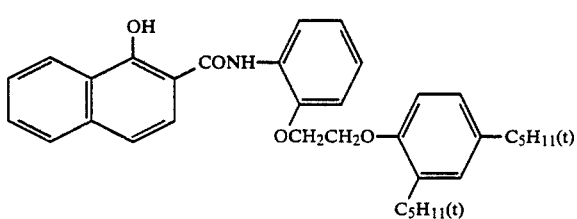 (10)
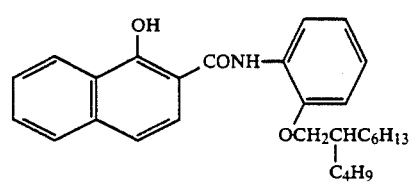 (11)

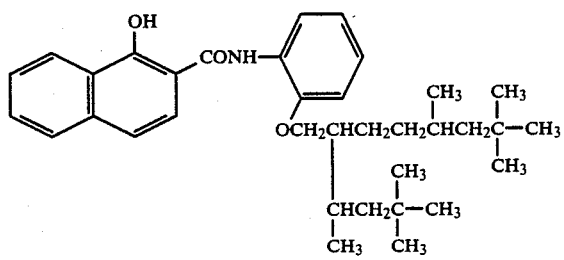
(12)
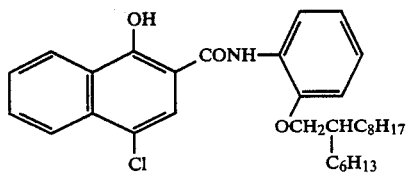
(13)
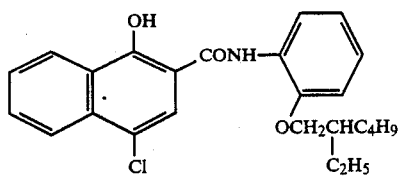
(14)
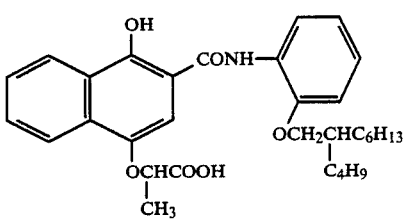
(15)
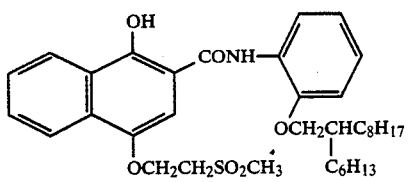
(16)
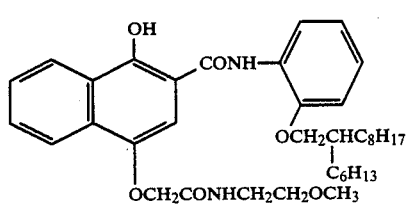
(17)
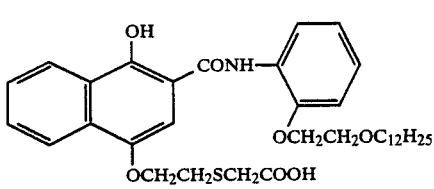
(18)
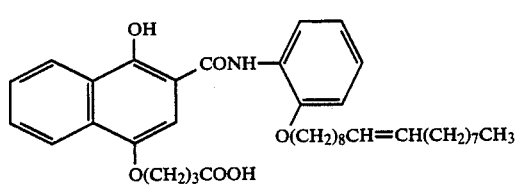
(19)

-continued
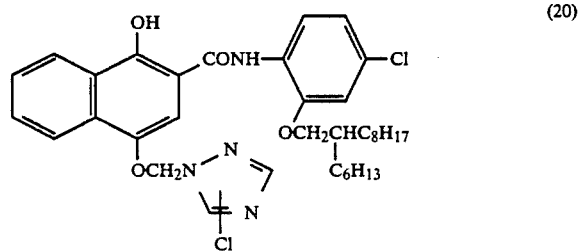
(20)
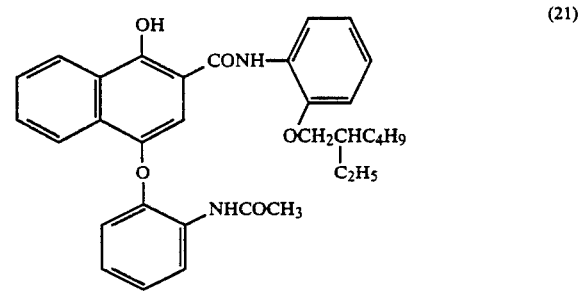
(21)
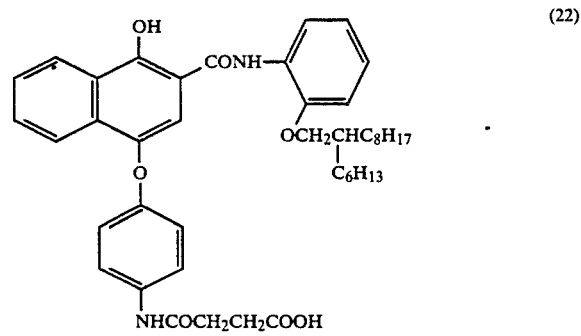
(22)
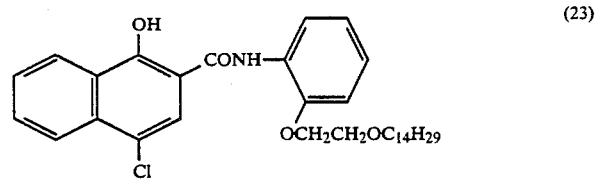
(23)
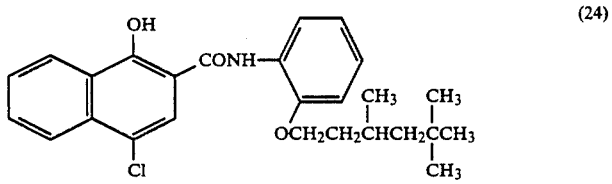
(24)
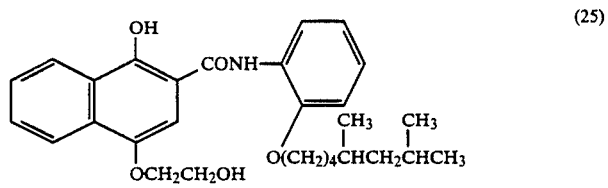
(25)
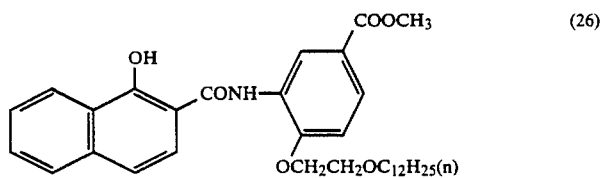
(26)

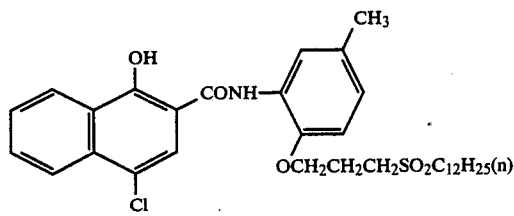

(27)

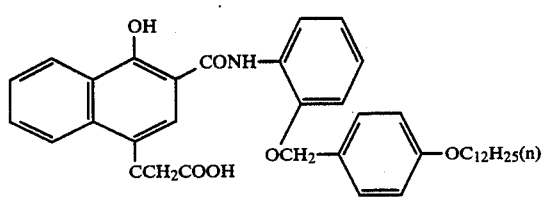

(28)

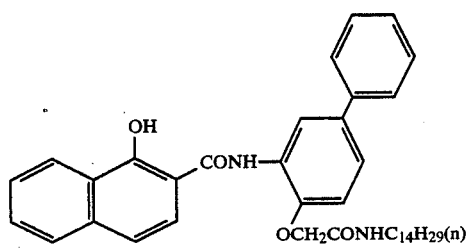

(29)

The compound represented by formula (I) can be prepared by processes as described, for example, in Japanese Patent Application (OPI) Nos. 117422/85, 18315/77, 90932/77, 52423/78, 105226/78, 48237/79, 66129/79, 32071/80, 65957/80, 1938/81, 12643/81, 27147/81, 126832/81, and 95346/83, and U.S. Pat. No. 3,488,193.

Examples of such a synthesis are described hereinafter.

SYNTHESIS EXAMPLE 1

Preparation of Exemplary Compound (1)

2.7 g of 2-hexyldecanol, 60 g of toluenesulfonic acid chloride, and 26.1 g of pyridine were dissolved in 250 ml of chloroform. The chloroform solution was then heat-refluxed for 6 hours. The reaction solution was washed with 300 ml of water three times and then concentrated to obtain 110 g of an oily 2-hexyldecyl paratoluene sulfonate.

45.4 g of 2-acetamidophenol, 110 g of 2-hexyldecyl paratoluene sulfonate thus obtained, and 62.1 g of potassium carbonate were admixed with 300 ml of dimethylfomamide. The admixture was then heated to a temperature of 70° C. with stirring for 5 hours. The reaction solution was admixed with 400 ml of ethyl acetate. The admixture was then washed with 500 ml of water three times and concentrated. The resulting concentrate was purified by means of a chromatographic column filled with silica gel with an n-hexane-ethyl acetate mixed solvent as a developing solvent to obtain 96.1 g of an oily 2-(2-hexyldecyloxy)acetanilide.

96.1 g of 2-(2-hexyldecyloxy)acetanilide thus obtained and 44 ml of concentrated hydrochloric acid were admixed with 250 ml of ethanol. The admixture was refluxed for 3 hours. The reaction solution was admixed with 300 ml of ethyl acetate. The admixture was washed with 400 ml of water three times and concentrated to obtain 69.2 g of an oily 2-(2-hexyldecyloxy)aniline.

23 g of phenyl 1-hydroxy-2-naphthoate and 35 g of 2-(2-hexyldecyloxy)aniline were heated to a temperature of 150° C. in a stream of nitrogen for 8 hours with stirring. The reaction solution ws then purified by means of a chromatographic column filled with silica gel with n-hexane as a developing solvent to obtain 32 g (oily) of the exemplary compound (1).

| | Elementary Analysis ($C_{33}H_{45}NO_3$) | | |
|---|---|---|---|
| | H (%) | C (%) | N (%) |
| Calculated | 9.00 | 78.69 | 2.78 |
| Found | 8.96 | 78.61 | 2.77 |

SYNTHESIS EXAMPLE 2

Preparation of Exemplary Compound (5)

An oily 3-(2-hexyldecyloxy)aniline was prepared in the same manner as used in Synthesis Example 1 except in that 2-acetamidophenol was replaced by 3-acetamidophenol. 19 g of phenyl 1-hydroxy-2-haphthoate and 24 g of 3-(2-hexyldecyloxy)aniline thus obtained were heated to a temperature of 140° C. with stirring for 4 hours. The reaction solution was then purified by means of a chromatographic column filled with silica gel with n-hexane as a developing solvent to obtain 24 g (oily) of the desired compound.

| | Elementary Analysis ($C_{33}H_{45}NO_3$) | | |
|---|---|---|---|
| | H (%) | C (%) | N (%) |
| Calculated | 9.00 | 78.69 | 2.78 |
| Found | 9.11 | 78.55 | 2.75 |

In the silver halide color photographic material of the present invention, any silver halide such as silver bromide, silver iodobromide, silver chlorobromide, silver chloroiodobromide, silver chloride, and silver chloroiodide may be used. In a high sensitivity light-sensitive material, silver iodobromide is preferably used. When silver iodobromide is used, the silver iodide content is generally 40 mol % or less, preferably 20 mol % or less, and more preferably 10 mol % or less.

The silver halide may be in the form of regular particle having a regular crystal form such as cubic, octahedral, and tetradecahedral, in the form of particle having an irregular crystal form, such as spherical, in the form of particle having a crystal defect such as twinning plane, or in the form of a composite thereof. A mixture of particles of various crystal forms may be used The above particulate silver halide may be in the form of finely divided particle having a particle diameter of about 0.1 μm or less or in the form of large size particle having a projected area diameter of up to about 10 μm. The silver halide particle size distribution is not particularly limited, and may be in the form of monodisperse emulsion having a narrow distribution or polydisperse emulsion having a wide distribution.

The above-mentioned emulsion layer may also comprise tabular particles having an aspect ratio of 5 or more.

The above-mentioned emulsion particles may have uniform crystal structure or the emulsion particles may comprise different inner and outer halogen composition. Alternatively, the above mentioned emulsion particles may have a laminar constitution. Such emulsion particles are disclosed in British Patent No. 1,027,146, U.S. Pat. Nos. 3,505,068 and 4,444,877, and Japanese Patent Application (OPI) No. 143331/85. Alternatively, silver halides having different compositions may be connected to each other by an epitaxial conjunction. Furthermore, silver halides may be connected to compounds other than silver halide such as silver thiocyanate and lead oxide.

The above-mentioned emulsion may be of the surface latent image type which forms latent images mainly on the surface thereof, or the internal latent image type which forms latent images mainly inside the particle. Alternatively, the above-mentioned emulsion may be of the type which forms latent images on the surface of the particle and inside the particle.

The silver halide photographic emulsion which may be used in the present invention can be prepared by any suitable known process as described in "I. Emulsion Preparation and Types", *Research Disclosure*, Vol. 176, RD No. 17643 (December, 1978), pp. 22-23, and Ibid., Vol. 187, RD No. 18716 (November, 1979), p. 648.

The photographic emulsion which may be used in the present invention can be prepared by any suitable process, such as those described in P. Glafkides, ed., *Chimie et Physique Photographique*, (Paul Montel, 1967), and G. F. Duffin, ed., *Photographic Emulsion Chemistry*, (The Focal Press, 1966), and V. L. Zelikman et al., ed., *Making and Coating Photographic Emulsion* (The Focal Press, 1964).

In the preparation of the photographic emulsion to be used in the present invention, various silver halide solvents such as ammonia, potassium thiocyanate, and a thioether, and a thion compound as described in U.S. Pat. No. 3,271,157, and Japanese Patent Application (OPI) Nos. 12360/76, 82408/78, 144319/78, 100717/79, and 155828/79 may be used.

A typical example of the monodisperse emulsion is an emulsion of particulate silver halide having a construction such that the average particle diameter is greater than about 0.1 μm and at least 95% by weight thereof is within ±40% of the average particle diameter. An emulsion of particulate silver halide having a construction such that the average particle diameter is from 0.25 to 2 μm and at least 95% by weight or particle number is within ±20% of the average particle diameter may be used in the present invention.

In the process of formation of particulate silver halide or physical aging, cadmium salt, zinc salt, lead salt, thallium salt, iridium salt or complex salt thereof, rhodium salt or complex salt thereof, or iron salt, or iron complex salt may be present.

The emulsion generally used in the present invention may be an emulsion which has been subjected to physical aging, chemical aging, and spectral sensitization. Examples of additives used in these processes are described in *Research Disclosure*, RD No. 17643 and Ibid., RD No. 18716. The places where these additives are referred to are summarized in the table shown below.

| Additives | RD 17643 | RD 18716 |
|---|---|---|
| 1. Chemical sensitizer | p. 23 | right column on p. 648 |
| 2. Sensitivity enhancement | | right column on p. 648 |
| 3. Spectral sensitizer, supersensitizer | pp. 23-24 | right column on p. 648 to right column on p. 649 |
| 4. Whitener | p. 24 | |
| 5. Antifogging agent and stabilizer | pp. 24-25 | right column on p. 649 |
| 6. Light absorber, filter dye, ultraviolet absorber | pp. 25-26 | right column on p. 649 to left column on p. 650 |
| 7. Stain inhibitor | right column on p. 25 | left column to right colum on p. 650 |
| 8. Color image stabilizer | p. 25 | |
| 9. Hardener | p. 26 | left column on p. 651 |
| 10. Binder | p. 26 | left column on p. 651 |
| 11. Plasticizer, lubricant | p. 27 | right column on p. 650 |
| 12. Coating assistant, surface active agent | pp. 26-27 | right column on p. 650 |
| 13. Anti-static agent | p. 27 | right column on p. 650 |

Typical examples of yellow couplers which may be used in the present invention include hydrophobic acylacetamide couplers having ballast groups. Specific examples of such yellow couplers are described in U.S. Pat. Nos. 2,407,210, 2,875,057, and 3,265,506. Diequivalent yellow couplers are preferably used in the present invention. Typical examples of such yellow couplers include oxygen atom-releasing type yellow couplers as described in U.S. Pat. Nos. 3,408,194, 3,447,928, 3,933,501, and 4,022,620 and nitrogen atom-releasing type yellow couplers as described in Japanese Patent Publication No. 10739/83, U.S. Pat. Nos. 4,401,752 and 4,326,024, Research Disclosure, RD No. 18053 (April, 1979), British Patent No. 1,425,020, and West German Patent Nos. 2,219,917, 2,261,361, 2,329,587, and 2,433,812. α-pivaloyl acetanilide couplers are excellent in the fastness of dye formed, especially to light. On the other hand, α-benzoyl acetanilide couplers can provide a high color density.

Examples of magenta couplers which may be used in the present invention include hydrophobic indazolone or cyanoacetyl, preferably 5-pyrazolone and pyrazoloazole couplers containing ballast groups. 5-pyrazolone couplers in which the 3-position is substituted by an arylamino group or acylamino group may be preferably used in the light of hue of the fye formed and color density. Typical examples of such a 5-pyrazolone couplers are described in U.S. Pat. Nos. 2,311,082, 2,343,703, 2,600,788, 2,908,573, 3,062,653, 3,152,896, and 3,936,015. Particularly preferred coupling-off groups for such a diequivalent 5-pyrazolone coupler include nitrogen atom-releasing groups as described in U.S. Pat. No. 4,310,619 and arylthio groups as described in U.S. Pat. No. 4,351,897. 5-pyrazolone couplers containing ballast groups as described in European Patent No. 73,636 can provide a high color density. Examples of pyrazoloazole couplers include pyrazolobenzimidazole as described in U.S. Pat. No. 3,061,432. Preferred examples of pyrazoloazole couplers include pyrazolo [5,1-c][1,2,4]triazole as described in U.S. Pat. No. 3,725,067, pyrazolotetrazole as described in *Research Disclosure*, Vol. 242, RD No. 24220 (June, 1984) and Japanese Patent Application (OPI) No. 33552/85, and pyrazolopyrazole as described in Ibid., Vol. 242, RD No. 24230 (June, 1984) and Japanese Patent Application (OPI) No. 43659/85. Imidazol[1,2-b] pyrazole as described in U.S. Pat. No. 4,500,630 may be preferably used in the light of less of yellow side absorption and fastness of the dye formed to light. Particularly preferred examples of pyrazoloazole couplers include pyrazolo [1,5-b][1,2,4]triazole as described in European Patent No. 119,860A.

Examples of cyan couplers which may be used in combination with the cyan couplers of the present invention include naphthol couplers as described in U.S. Pat. No. 2,474,293. Typical examples of preferred cyan couplers include oxygen atom-releasing type diequivalent naphthol couplers as described in U.S. Pat. Nos. 4,052,212, 4,146,396, 4,228,233, and 4,296,200. Specific examples of phenol couplers are described in U.S. Pat. Nos. 2,369,929, 2,801,171, 2,772,162, and 2,895,826. Cyan couplers which are fast to moisture and heat may be preferably used in combination with the cyan couplers of the present invention. Typical examples of such cyan couplers include phenol couplers containing a phenyl ureido group at the 2-position and an acyl amino group at the 5-position.

In order to correct undesired absorption by the dye formed, a color negative light-sensitive material preferably comprises a colored coupler to provide masking. Examples of colored couplers are described in Article VII-G of *Research Disclosure*, RD No. 17643.

The light-sensitive material of the present invention may comprise a coupler having a proper diffusibility to improve graininess. Specific examples of magenta couplers suitable for this purpose are described in U.S. Pat. No. 4,366,237 and British Pat. No. 2,125,570. Specific examples of yellow, magenta, and cyan couplers suitable for this purpose are described in European Pat. No. 96,570 and West German Patent (OLS) No. 3,234,533.

The dye-forming couplers of the present invention and the above-mentioned special couplers may form dimers or higher polymers. Typical examples of polymerized dye-forming couplers are described in U.S. Pat. Nos. 3,451,820 and 4,080,211. Specific examples of polymerized magenta couplers are described in British Pat. No. 2,102,173 and U.S. Pat. No. 4,367,282.

A coupler which releases a photographically useful residue upon coupling may be preferably used in the present invention. Useful DIR couplers which releases a development inhibitor are described in the patents cited in Article VII-F of *Research Disclosure*, RD No. 17643.

The objects of the present invention can be accomplished by using the cyan coupler of the present invention in an amount of from 0.002 to 0.5 mol per mol of light-sensitive silver halide in the layer into which it is incorporated. When a conventional cyan coupler is used in combination with the cyan coupler of the present invention, the amount of the cyan coupler of the present invention is preferably more than 10% based on the total weight of cyan couplers.

The layer to which the cyan coupler of the present invention is incorporated is usually a silver halide light-sensitive emulsion layer, however, it may be an auxiliary layer adjacent to the emulsion layer. The cyan coupler of the present invention may be incorporated in either blue-, red-, or green-sensitive layer (and/or a layer adjacent thereto), although it is usually incorporated in a red-sensitive (and/or adjacent layer thereto).

The couplers of the present invention and the couplers which may be used in combination therewith is incorporated into the light-sensitive material by an oil-in-water dispersion process. In oil-in-water dispersion processes, the coupler is dissolved in either a high boiling organic solvent having a b.p. of 175° C. or more or a low boiling solvent, i.e., assistant solvent or a mixture thereof. The solution thus obtained is then finely dispersed in water or an aqueous medium such as aqueous solution of gelatin in the presence of a surface active agent. Examples of such a high boiling organic solvent are described in U.S. Pat. No. 2,322,027. The dispersion may involve phase inversion. Before being subjected to coating, the dispersion thus obtained may be subjected to distillation, noodle rinsing, or ultrafiltration to remove or reduce the assistant solvent.

The coupler of the present invention overcomes the defect (which is inherent to such a type of coupler) of shifting the wavelength of the hue (due to dye coagulation) to a shorter wavelength.

The light-sensitive material of the present, invention may comprise as a color fog inhibitor, a color mixing inhibitor, a hydroquinone derivative, an aminophenol derivative, an amine, a gallic acid derivative, a catechol derivative, an ascorbic acid derivative, a non-coloring coupler, or a sulfonamide phenol derivative.

The light-sensitive material of the present invention may comprise various discoloration inhibitors. Typical examples of such discoloration inhibitors include a hydroquinone, a 6-hydroxy chroman, a 5-hydroxy cumarane, a spirochroman, a p-alkoxyphenol, a hindered phenol such as a bis phenol, a gallic acid derivative, a methylene dioxybenzene, an amino phenol, a hindered amine, and an ether or an ester derivative obtained by silylating or alkylating the phenolic hydroxyl group of these compounds. Alternatively, metal complexes such as (bis-salicylaldoximato) nickel complex and (bis-N,N-dialkyldithiocarbamato)nickel complex may be used.

The light-sensitive material of the present invention preferably comprise appropriate auxiliary layers such as a protective layer, an intermediate layer, a filter layer, an anti-halation layer, and a back layer, in addition to the silver halide emulsion layer.

The color photographic material of the present invention may be subjected to a conventional development process, described, for example, in pp. 28–29 of Research Disclosure, RD No. 17643 and the left column to the right column on p. 651 of Ibid., RD No. 18716. The present color photographic material is subjected to bleaching and fixing or blixing after development, and generally subjected to rinsing or stabilization after development, blix, or fixing.

Typical example of the aromatic primary amine-developing agent is a p-phenylene diamine compound such as 3-methyl-4-amino-N,N-diethylaniline, 3-methyl-4-amino-N-ethyl-N-3-hydroxylethylaniline, 3-methyl-4-amino-N-ethyl-N-8-methanesulfonamide ethylaniline, 3-methyl-4-amino-N-ethyl-N-8-methoxyethylaniline, and sulfates, hydrochlorides, and p-toluenesulfonates thereof.

As bleaching agent there may be used a compound of a polyvalent metal such as iron (III), cobalt (III), chromium (VI), and copper (II), a peroxide, a quinone, and nitroso compound. Typical examples of such a bleaching agent include ferricyanides, dichromates, organic complex salts of iron (III) or cobalt (III), aminopolycarboxylic acids such as ethylene diamine tetraacetic acid, diethylene triamine pentaacetic acid, nitrilo triacetic acid, 1,3-diamino-2-propanol tetraacetic acid; complex salts of organic acids such as citric acid, tartaric acid, and malic acid; persulfates; manganates; and nitrosophenol. Among these bleaching agents, iron (III) ethylene diamine tetraacetate and persulfates are preferably used, in view of rapidness of processing and pollution consideration. Furthermore, ethylene diamine tetraacetic acid-iron (III) complex salt is useful in single bleaching bath, particularly in combined blix bath.

In order to save water, rinsing is generaly conducted such that two or more baths are operated in counterflow manner. Typical examples of stabilization include multistage counterflow stabilization as described in Japanese Patent Application (OPI) No. 8543/82 rather than rinsing. Such a process needs 2 to 9 counterflow baths. The stabilization bath can comprise various compounds to stabilize images. Typical examples of such compounds include various buffers for adjusting the pH of the film (e.g., 3 to 8) (e.g., a borate, a metaborate, borax, a phosphate, a carbonate, a potassium hydroxide, sodium hydroxide, an aqueous ammonia, a monocarboxylic acid, a dicarboxylic acid, a polycarboxylic acid, and the like may be used in combination) and formalin. Besides the above compounds, various additives such as a water softener (e.g., an inorganic phosphoric acid, an amino polycarboxylic acid, an organic phosphoric acid, an amino polyphosphonic acid, and a phosphonocarboxylic acid), germicide (e.g., a benzoisothiazolinone, isothiazolone, a 4-thiazolinebenzimidazole, and a halogenated phenol), a surface active agent, a fluorescent brightening agent, and a hardner may be used. Two or more compounds which are used either in the same or different purpose may be used in combination.

Preferred examples of a film pH adjustor which may be used after the treatment include various ammoinum salts such as ammonium chloride, ammonium nitrate, ammonium sulfate, ammonium phosphate, ammonium sulfite, and ammonium thiosulfate.

The present invention can be applied to various color-image-forming light-sensitive materials. Typical examples of color light-sensitive materials to which the present invention can be applied include color reversal film for slide projection and television and color reversal paper. The present invention can also be applied to a black-and-white light-sensitive material utilizing a mixture of three color couplers as described in Research Disclosure, Vol. 171, RD No. 17123 (July, 1978).

The present invention will be further illustrated in the following examples, but the present invention should not be construed as being limited thereto.

EXAMPLE 1

Light-sensitive material specimens 101 to 110 were prepared by coating a cellulose triacetate support with compositions shown below. The coupler to be contained in the first layer is shown in Table 1.

| 1st layer | |
|---|---|
| Silver iodobromide emulsion silver iodide: 4 mol %) | 1.44 g/m$^2$ (calculated in terms amount of silver) |
| Sensitizing dye I | $4.5 \times 10^{-4}$ mol per mol of silver |
| Sensitizing dye II | $1.5 \times 10^{-4}$ mol per mol of silver |
| Coupler (shown in TABLE 1) | $6.0 \times 10^{-2}$ mol per mol of silver |

2nd layer: protective layer

A gelatin layer containing a particulate polymethyl methacrylate (diameter: about 1.5 μm).

Besides the above compositions, a gelatin hardener H-1 and a surface active agent were added to each Compounds used for the preparation of the specimens Sensitizing dye I: pyridinium anhydro-5,5'-dichloro-3,3'-di-(γ-sulfopropyl)-9-ethyl-thiacarbocyanine hydroxide Sensitizing dye II: triethylamine anhydro-9-ethyl-3,3'-di-(γ-sulfopropyl)-4,5,4'-5'-dibenzothiacarbocyanine hydroxide

H-1: $(CH_2=CHSO_2CH_2CONHCH_2)_2$

For the measurement of sensitometry, the specimens 101 to 106 were exposed to light. The specimens thus exposed were then subjected to the following development (A) at a temperature of 38° C.:

| 1. Color development | 3 min. 15 sec. |
|---|---|
| 2. Bleaching | 6 min. 30 sec. |
| 3. Rinsing with water | 3 min. 15 sec. |
| 4. Fixing | 4 min. 20 sec. |
| 5. Rinsing with water | 3 min. 15 sec. |
| 6. Stabilization | 1 min. 5 sec. |

The composition of the treatment solutions used in the above processes were as follows:

| Color developing solution: | |
|---|---|
| Sodium nitrilo triacetate | 1.0 g |
| Sodium sulfite | 4.0 g |
| Sodium carbonate | 30.0 g |
| Potassium bromide | 1.4 g |
| Hydroxyl amine sulfate | 2.4 g |
| 4-(N-ethyl-N-β-hydroxyethylamino)-2-methylaniline sulfate | 4.5 g |

Water was added to the above composition in an amount such that the volume thereof reached 1 liter.

| Bleaching bath: | |
|---|---|
| Ammonium bromide | 160.0 g |

-continued

Bleaching bath:

| | |
|---|---|
| Aqueous ammonia (28%) | 25.0 ml |
| Ethylene diamine tetraacetate sodium iron salt | 130.0 g |
| Glacial acetic acid | 14.0 ml |

Water was added to the above composition in an amount such that the volume thereof reached 1 liter.

Fixing bath:

| | |
|---|---|
| Sodium tetrapolyphosphate | 2.0 g |
| Sodium sulfite | 4.0 g |
| Ammonium thiosulfate (70%) | 175.0 ml |
| Sodium biphosphite | 4.6 g |

Water was added to the above composition in an amount such that the volume thereof reached 1 liter.

Stabilizing solution:

Formalin (37 wt % formaldehyde solution); 8.0 ml

Water was added to the formalin in an amount such that the volume thereof reached 1 liter.

The same specimens as used hereinabove were then subjected to the development (B) in the same manner as used in the development (A), except that the bleaching bath was changed to the following composition. This bleaching bath simulated the state of fatigue obtained after treatment of a large amount of light-sensitive materials.

Development (B)

Bleaching bath:

(D-1)

| | |
|---|---|
| Ammonium bromide | 160.0 g |
| Aqueous ammonia (28%) | 7.1 ml |
| Ethylene diamine tetraacetate sodium iron salt | 117 g |
| Glacial acetic acid | 14 ml |

Water was added to the above composition in an amount such that the volume thereof reached 900 ml.

(D-2)

| | |
|---|---|
| Ethylene diamine tetraacetate sodium iron salt | 130 g |

Water was added to the above composition in an amount such that the volume thereof reached 1 liter.

Steel wool was put into (D-2), and the admixture was hermetically sealed. The admixture was allowed to stand so that Fe (III)-EDTA was converted to Fe (II)-EDTA. 100 ml of the thus-obtained solution was added to (D-1) to obtain the bleaching bath for the development (B).

The specimens 101 to 110 which had been subjected to the development (A) and the development (B) were measured for density by red light and green light. (A self-recording densitometer available from Fuji Photo Film Co., Ltd. was used.)

The results are shown in Table 1.

TABLE 1

| Specimen No. | 1st Layer Coupler | Dye Remaining | Relative Sensitivity | Ratio of Green Density at Red Density of 0.5 | Ratio of Green Density at Red Density of 2.0 |
|---|---|---|---|---|---|
| 101* | A | 72% | 100% | 16% | 16% |
| 102* | B | 98% | 120% | 18% | 30% |
| 103* | C | 98% | 129% | 17% | 32% |
| 104* | D | 72% | 100% | 16% | 16% |
| 105* | E | 99% | 100% | 28% | 16% |
| 106 | Exemplary coupler (1) | 99% | 132% | 14% | 15% |
| 107 | Exemplary coupler (2) | 99% | 129% | 16% | 17% |
| 108 | Exemplary coupler (7) | 98% | 135% | 15% | 14% |
| 109 | Exemplary coupler (13) | 97% | 132% | 16% | 15% |
| 110 | Exemplary coupler (23) | 99% | 138% | 14% | 15% |

*comparative example

In Table 1, dye remaining is defined by the equation:

$$\text{Dye remaining} = \frac{\text{Maximum red density at development (B)}}{\text{Maximum red density at development (A)}} \times 100$$

Relative sensitivity in Table 1 is represented by the antilogarithm of relative value of the reciprocal of the exposure required to provide the density corresponding to [minimum density+0.2]. The ratio of green density at red density of 0.5 and the ratio of green density at red density of 2.0 are defined by the equations:

$$\left(\begin{array}{c}\text{Ratio of green density}\\\text{at red density of 0.5}\end{array}\right) = \left(\begin{array}{c}\text{green density at red}\\\text{density of 0.5/0.5}\end{array}\right) \times 100$$

$$\left(\begin{array}{c}\text{Ratio of green density}\\\text{at red density of 2.0}\end{array}\right) = \left(\begin{array}{c}\text{green density at red}\\\text{density of 2.0/2.0}\end{array}\right) \times 100$$

As can be seen Table 1, the specimens of the present invention show less reduction in red density in a fatigued bleaching bath, provide a higher sensitivity, and also show a less undesirable absorption of green range and a less change in absorption of green range due to change in red density.

Comparative couplers

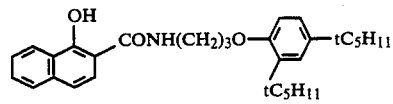
A

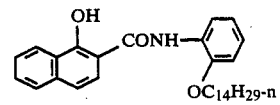
B

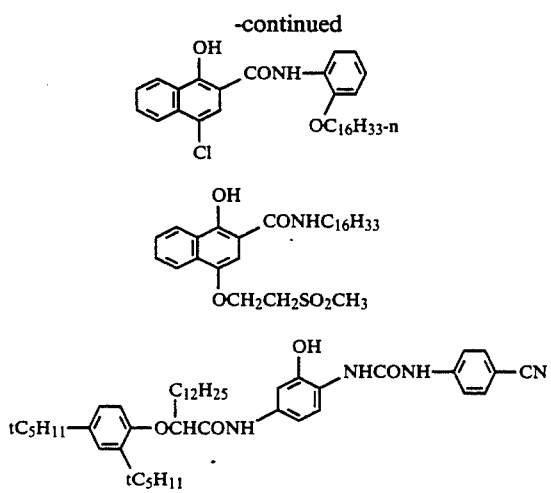

-continued

C

D

E

EXAMPLE 2

Specimens 201 to 205 were prepared in the same manner as used in Example 1 except that the couplers to be used in the first layer were changed. For the measurement of sensitometry, these specimens were then exposed to light in the same manner as used in Example 1. The specimens thus exposed were subjected to each of development (A) and development (B) at a temperature of 38° C.

Comparative Coupler F

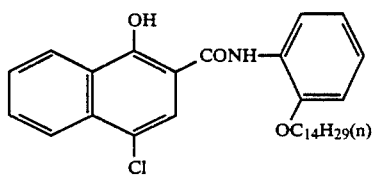

The results are shown in Table 2.

TABLE 2

| Specimen No. | 1st Layer Coupler | Dye Remaining | Relative Sensitivity | Ratio of Green Density at Red Density of 0.5 | Ratio of Green Density at Red Density of 2.0 |
|---|---|---|---|---|---|
| 201* | D | 72% | 100% | 16% | 16% |
| 202* | E | 96% | 89% | 30% | 16% |
| 203* | F | 96% | 102% | 16% | 30% |
| 204 | Exemplary coupler (13) | 97% | 132% | 16% | 15% |
| 205 | Exemplary coupler (16) | 98% | 126% | 15% | 16% |

*comparative example

As is clear from Table 2, the present specimens 204 to 205 attain the desired objects of the invention.

Comparative couplers

EXAMPLE 3

A multilayer color light-sensitive material 301 was prepared by coating a cellulose triacetate film with the following layers:

1st layer: antihalation layer

A gelatin layer containing black colloidal silver.

2nd layer: intermediate layer

A gelatin layer containing an emulsion dispersion of 2,5-di-t-octyl hydroquinone.

3rd layer: 1st red-sensitive emulsion layer

| | |
|---|---|
| Silver iodobromide (silver iodide: 5 mol %) | 1.6 g/m² (calculated in terms of amount of silver) |
| Sensitizing dye I | 4.5 × 10⁻⁴ mol per mol of silver |
| Sensitizing dye II | 1.5 × 10⁻⁴ mol per mol of siler |
| Coupler EX-1 | 0.03 mol per mol of silver |
| Coupler EX-2 | 0.003 mol per mol of silver |
| Coupler EX-3 | 0.0008 mol per mol of silver |

4th layer: 2nd red-sensitive emulsion layer

| | |
|---|---|
| Silver iodobromide (silver iodide: 10 mol %) | 1.4 g/m² (calculated in terms of amount of silver) |
| Sensitizing dye I | 3 × 10⁻⁴ mol per mol of silver |
| Sensitizing dye II | 1 × 10⁻⁴ mol per mol of silver |
| Coupler D | 0.022 mol per mol of silver |
| Coupler EX-2 | 0.0016 mol per mol of silver |

5th layer: intermediate layer

Same as the 2nd layer

6th layer: 1st green-sensitive emulsion layer

| | |
|---|---|
| Silver iodobromide emulsion (silver iodide: 4 mol %) | 1.2 g/m² (calculated in terms of amount of silver) |
| Sensitizing dye III | 5 × 10⁻⁴ mol per mol of silver |
| Sensitizing dye IV | 2 × 10⁻⁴ mol per mol of silver |
| Coupler EX-4 | 0.05 mol per mol of silver |
| Coupler EX-5 | 0.008 mol per mol of silver |
| Coupler EX-6 | 0.0018 mol per mol of silver |

7th layer: 2nd green-sensitive emulsion layer

| | |
|---|---|
| Silver iodobromide emulsion (silver iodide: 8 mol %) | 1.3 g/m² (calculated in terms of amount of silver) |
| Sensitizing dye III | 3 × 10⁻⁴ mol per mol of silver |
| Sensitizing dye IV | 1.2 × 10⁻⁴ mol per mol of silver |
| Coupler EX-7 | 0.017 mol per |

-continued

| | mol of silver |
|---|---|
| Coupler EX-8 | 0.003 mol per mol of silver |

8th layer: yellow filter layer

A gelatin layer containing an emulsion dispersion of yellow colloidal silver and 2,5-di-t-octyl hydroquinone in an aqueous solution of gelatin.

9th layer: 1st blue-sensitive emulsion layer

| Silver iodobromide emulsion (silver iodide: 6 mol %) | 0.7 g/m² (calculated in terms of amount of silver) |
|---|---|
| Coupler EX-9 | 0.25 mol per mol of silver |
| Coupler EX-10 | 0.015 mol per mol of silver |

10th layer: 2nd blue-sensitive emulsion layer

| Silver iodobromide emulsion (silver iodide: 6 mol %) | 0.6 g/m² (calculated in terms of amount of silver) |
|---|---|
| Coupler EX-9 | 0.06 mol per mol of silver |

-continued

11th layer: 1st protective layer

| A gelatin layer containing: | |
|---|---|
| Silver iodobromide (silver iodide: 1 mol %; average particle diameter: 0.07 μm) | 0.5 g/m² (calculated in terms of amount of silver) |
| An emulsion dispersion of an ultraviolet absorber UV-1 | |

12th layer: 2nd protective layer

A gelatin layer containing particulate polymethylmethacrylate (diameter: about 1.5 μm).

Besides the above compositions, a gelatin hardener H-1 and surface active agents were added to each layer.

Compounds used for the preparation of the specimen 301

Sensitizing dye III: sodium salt of anhydro-9-ethyl-5,5'-dichloro-3,3'-di-(γ-sulfopropyl)oxacarbocyanine Sensitizing dye IV: sodium salt of anhydro-5,6,5',6'-tetrachloro-1,1'-diethyl-3,3'-di-{β-[β-(γ-sulfopropoxy)ethoxy]ethylimidazolo}carbocyanine hydroxide

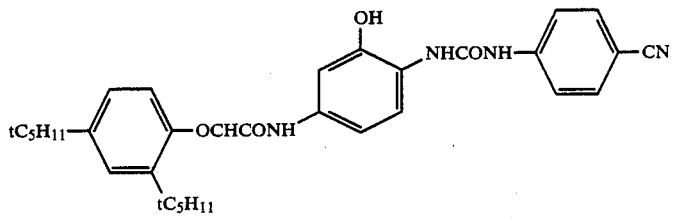

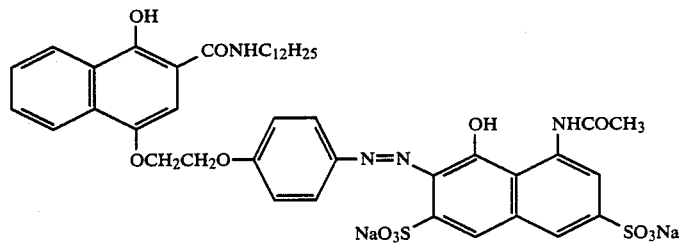

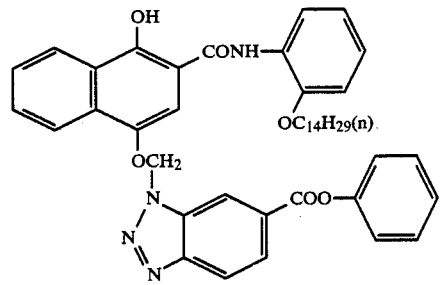

-continued
EX-4
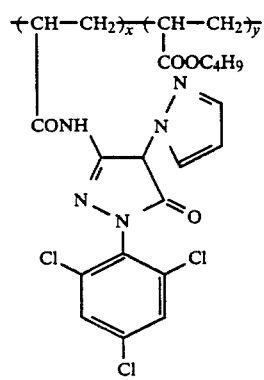
x/y = 50/50
Molecular weight: about 30,000
Coupler EX-5
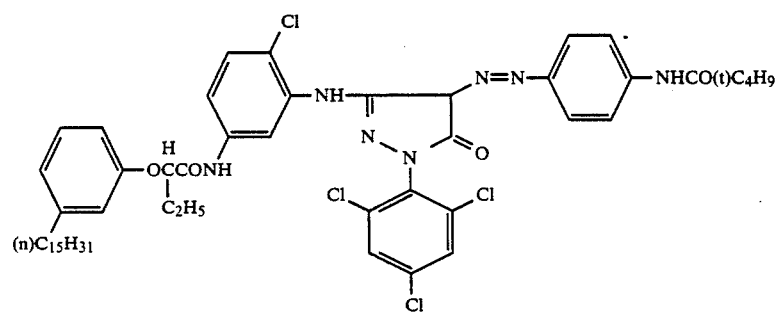
EX-6
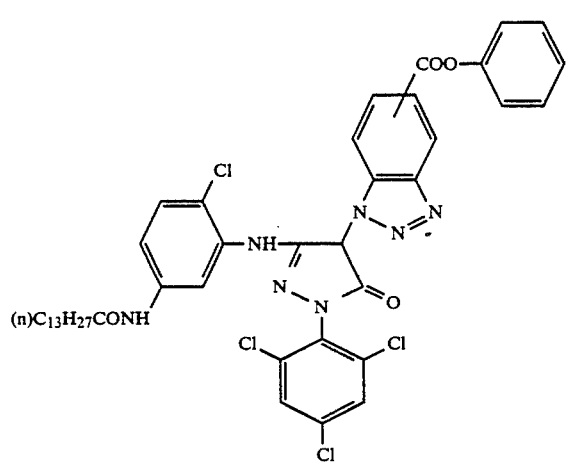
Coupler EX-7
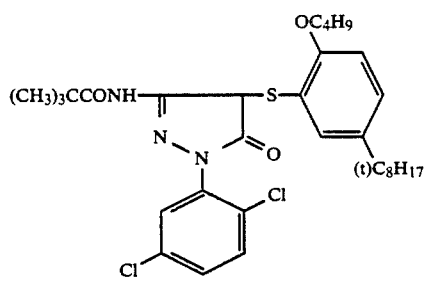

-continued

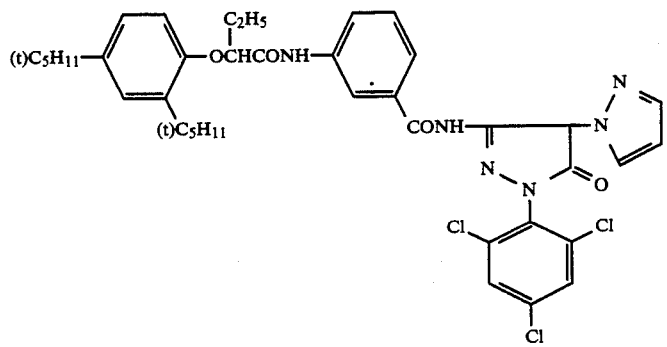
Coupler EX-8

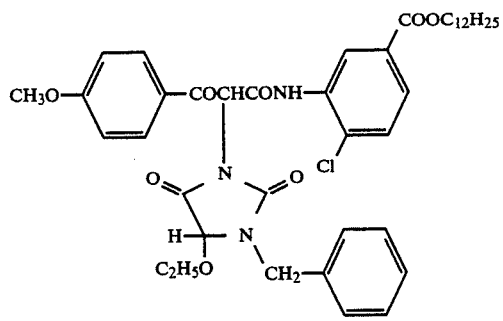
Coupler EX-9

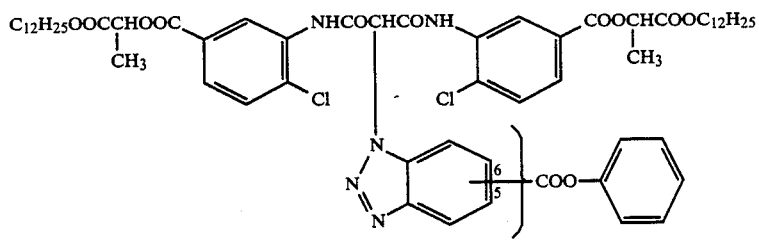
EX-10

(a mixture of the compound substituted at 5- or 6-position)

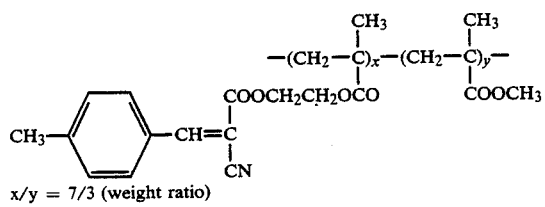
UV-1 x/y = 7/3 (weight ratio)

Specimens 302 to 308 were prepared by replacing the coupler (D) of the specimen 301 with the same mol of another coupler as shown in Table 3.

For the measurement of sensitometry, the specimens 301 to 308 were exposed to light. The specimens thus exposed were then subjected to development with a fresh solution (Development (A)) or a solution which had been deteriorated after a prolonged continuous operation (Development (B)). The specimens thus treated were measured for density by red light. The results are shown in Table 3.

TABLE 3

| Specimen No. | 4th Layer Coupler | Relative Sensitivity at Development (A) | Density at Development (B) at Exposure Giving Density of 1.5 at Development (A) |
|---|---|---|---|
| 301* | D | 100 | 1.28 |
| 302* | E | 87 | 1.46 |
| 303* | F | 98 | 1.47 |
| 304 | Exemplary coupler (13) | 135 | 1.48 |
| 305 | Exemplary coupler (16) | 132 | 1.48 |
| 306 | Exemplary coupler (18) | 138 | 1.47 |
| 307 | Exemplary coupler (21) | 129 | 1.46 |
| 308 | Exemplary coupler (22) | 132 | 1.47 |

*comparative example

As is clear from Table 3, the specimens 304 to 305 of the present invention provide a higher sensitivity than the specimens 301 to 303 comprising the comparative couplers (D) to (F). The specimens of the present invention also show little reduction in color density in a fatigued bleaching bath.

While the invention has been described in detail and with reference to specific embodiments thereof, it will be apparent to one skilled in the art that various changes and modifications can be made therein without departing from the spirit and scope thereof.

What is claimed is:

1. A method for producing a photographic image which comprises developing an exposed silver halide color photographic light-sensitive material with a developer comprising an aromatic primary amine-developing agent, wherein said silver halide color photographic light-sensitive material has at least one light-sensitive silver halide emulsion layer provided on a support and said photographic material contains at least one non-diffusible, oil-soluble cyan dye-forming coupler represented by formula (I)

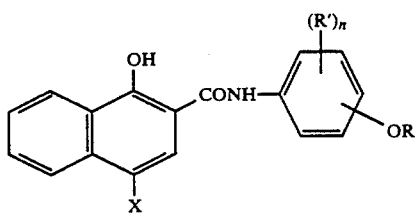

wherein R represents a substituted or unsubstituted branched alkyl group or an alkyl group substituted with other than an alkyl group, said R containing 6 or more carbon atoms and said R not being substituted with (1) a carboxyl group which is not substituted, (2) a sulfo group which is not substituted, (3) a carboxyl group which is substituted with a metal atom, (4) a carboxyl group which is substituted with an —NH$_4$ group, (5) a sulfo group which is substituted with a metal atom of (6) a sulfo group which is substituted with an —NH$_4$ group; X represents a hydrogen atom or a non-photographically-useful group which can be released therefrom upon coupling with an oxidized form of an aromatic primary amine developing agent; R' represents a group which can be substituted at a phenyl nucleus other than a group which can be represented by OR; and n is an integer of from 0 to 4, said coupler being incorporated into the emulsion by an oil-in-water dispersion process.

2. A silver halide color photographic light-sensitive material having at least one light-sensitive silver halide emulsion layer provided on a support and said photographic material contains at least one non-diffusible, oil-soluble cyan dye-forming coupler represented by formula (I)

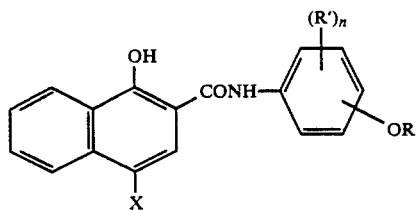

wherein R represents a substituted or unsubstituted branched alkyl group, or an alkyl group substituted with other than an alkyl group, said R containing 6 or more carbon atoms and said R not being substituted with (1) a carboxyl group which is not substituted, (2) a sulfo group which is not substituted, (3) a carboxyl group which is substituted with a metal atom, (4) a carboxyl group which is substituted with an —NH$_4$ group, (5) a sulfo group which is substituted with a metal atom or (6) a sulfo group which is substituted with an —NH$_4$ group; X represents a hydrogen atom or a non-photographically-useful group which can be released therefrom upon coupling with an oxidized form of an aromatic primary amine developing agent: R' represents a group which can be substituted on a phenyl nucleus other than a group which can be represented by OR; and n is an integer of from 0 to 4, said coupler is incorporated into the emulsion by an oil-in-water dispersion process.

3. A silver halide color photographic light-sensitive material as in claim 2, wherein the substituent for R is selected from the group consisting of an alkenyl group, alkynyl group, cycloalkyl group, aromatic group, heterocyclic group, halogen atom, aliphatic oxy group, aromatic oxy group, heterocyclic oxy group, aliphatic thio hydroxy group, cyano group, aliphatic sulfonyl group, aromatic sulfonyl group, heterocyclic sulfonyl group, aliphatic sulfinyl group, aromatic sulfinyl group, heterocyclic sulfinyl group, aliphatic oxycarbonyl group, acyloxy group, acyl group, carbamoyl group, sulfamoyl group, carbonamido group, sulfonamido group, ureido group, sulfamoylamino group, aliphatic oxycarbonylamino group, and carbamoyloxy group.

4. A silver halide color photographic light-sensitive material as in claim 2, wherein X is selected from the group consisting of a hydrogen atom, halogen atom, —COOM, —SO$_3$M (wherein M represents H, an alkali metal atom, or NH$_4$), aliphatic oxy group, aromatic oxy group, heterocyclic oxy group, aliphatic thio group, aromatic thio group, acyloxy group, carbonamide group, aliphatic sulfonyloxy group, aromatic sulfonyloxy group, aliphatic oxycarbonyloxy group, aliphatic thiocarbonylamino group, carbamoyloxy group, and heterocyclic group is connected to the coupling active position of the coupler of formula (I) by a nitrogen atom.

5. A silver halide color photographic light-sensitive material as in claim 3, wherein said aliphatic group represents a substituted or unsubstituted straight-chain, branched, or cyclic alkyl, alkenyl, or alkynyl group; said aromatic group represents a substituted or unsubstituted monocyclic or condensed aryl group; and said heterocyclic group represents a substituted or unsubstituted 5- or 6-membered monocyclic group containing at least one of an N, S, or O atom or condensed heterocyclic group thereof.

6. A silver halide color photographic light-sensitive material as in claim 4, wherein said aliphatic group represents a substituted or unsubstituted straight-chain, branched, or cyclic alkyl, alkenyl, or alkynyl group; said aromatic group represents a substituted or unsubstituted monocyclic or condensed aryl group; and said heterocyclic group represents a substituted or unsubstituted 5- or 6-membered monocyclic group containing at least one of an N, S, or O atom or condensed heterocyclic group thereof.

7. A silver halide color photographic light-sensitive material as in claim 2, wherein said R contains at most 30 carbon atoms.

8. A silver halide color photographic light-sensitive material as in claim 2, wherein said R is a substituted or unsubstituted branched alkyl group.

9. A silver halide color photographic light-sensitive material as in claim 2, wherein the group —OR in formula (I) is present at the ortho-position of the benzene nucleus to which —OR is substituted.

10. A silver halide color photographic light-sensitive material as in claim 2, wherein said R' represents an alkenyl group, alkynyl group. cycloalkyl group, aromatic group, heterocyclic group, halogen atom. aliphatic oxy group, aromatic oxy group, heterocyclic oxy group, aliphatic thio group, aromatic thio group, heterocyclic thio group, hydroxy group, cyano group, aliphatic sulfonyl group, aromatic sulfonyl group, heterocyclic sulfonyl group, aliphatic sulfinyl group, aromatic sulfinyl group, heterocyclic sulfinyl group, aliphatic oxycarbonyl group, acyloxy group, acyl group, carbamoyl group, sulfamoyl group, carbonamido group, sulfonamido group, ureido group, sulfamoylamino group, aliphatic oxycarbonylamino group, and carbamoyloxy group.

11. A silver halide color photographic light-sensitive material as in claim 10, wherein said aliphatic group represents a substituted or unsubstituted straight-chain, branched, or cyclic alkyl, alkenyl, or alkynyl group; said aromatic group represents a substituted or unsubstituted monocyclic or condensed aryl group; and said heterocyclic group represents a substituted or unsubstituted 5- or 6-membered monocyclic group containing at least one of an N, S, or O atom or condensed heterocyclic group thereof.

12. A silver halide color photographic light-sensitive material as in claim 2, wherein said coupler is incorporated into a light-sensitive silver halide emulsion layer or to an auxiliary layer adjacent thereto.

13. A silver halide color photographic light-sensitive material as in claim 12, wherein said cyan coupler is incorporated in an amount of from 0.002 to 0.5 mol per mol of light-sensitive silver halide.

14. A silver halide color photographic light-sensitive material as in claim 12, wherein said silver halide emulsion layer is a red-sensitive silver halide emulsion layer.

15. A silver halide color photographic light-sensitive material as in claim 2, wherein said aromatic primary amine-developing agent is a p-phenylene diamine compound.

* * * * *